(12) United States Patent
Sugamura et al.

(10) Patent No.: US 6,838,551 B2
(45) Date of Patent: Jan. 4, 2005

(54) PROTEIN AMSH AND CDNA THEREOF

(75) Inventors: Kazuo Sugamura, Miyagi (JP);
Nobuyuki Tanaka, Miyagi (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/671,572

(22) Filed: Sep. 29, 2003

(65) Prior Publication Data

US 2004/0096954 A1 May 20, 2004

Related U.S. Application Data

(62) Division of application No. 09/831,452, filed as application No. PCT/JP99/06309 on Nov. 12, 1999.

(30) Foreign Application Priority Data

Nov. 12, 1998 (JP) .......................... 10-322674

(51) Int. Cl.⁷ .................. C12P 21/06; C07H 17/00; C07K 14/00
(52) U.S. Cl. .................. 530/350; 435/69.1; 435/320.1
(58) Field of Search .................. 530/350; 435/69.1, 435/320.1

(56) References Cited

U.S. PATENT DOCUMENTS 6,673,570 B1 * 1/2004 Itoh et al. .................. 435/69.1
2002/0156012 A1 * 10/2002 Lyapina et al. .............. 514/12
2003/0166243 A1 * 9/2003 Cope et al. .................. 435/226

OTHER PUBLICATIONS

NCBI Accession No. BAB31909, Feb. 8, 2001.*
Kazuo Sugamura et al., "Possible involvement of a novel STAM-associated molecule "AMSH" in intracellular signal transduction mediated by cytokines", J. Biol. Chem., vol. 274, No. 27, pp. 19129–19135, Jul. 1999.
Wei Yu et al., "Large-scale concatenation cDNA sequencing", Genome Research, vol. 7, No. 4, pp. 353–358, 1997.
Meredith A. Wentland et al., "A "double adaptor" method for improved shotgun library construction", Analytical Biochemistry, vol. 236, No. 1, pp. 107–113, 1996.
K. Sugamura et al., "STAM, signal transducing adaptor molecule, is associated with Janus kinases and involved in signaling for cell growth and c-myc induction", Immunity, vol. 6, No. 4, pp. 449–457, 1997.

* cited by examiner

*Primary Examiner*—Janet Andres
*Assistant Examiner*—Rachel K. Hunnicutt
(74) *Attorney, Agent, or Firm*—Wenderoth, Lind & Ponack, L.L.P.

(57) ABSTRACT

This application provides a human protein AMSH having the amino acid sequence of SE ID No. 1 which is a novel signal transduction molecule interacting with the SH3 domain of cytokine based signal transduction molecule STAM; a gene encoding the above AMSH; a cDNA having the nucleotide sequence of SEQ ID No. 2; and antibody against AMSH.

4 Claims, No Drawings

PROTEIN AMSH AND CDNA THEREOF

This application is a divisional of Ser. No. 09/831,452 filed Jun. 10, 2001, which is a U.S. national stage of International Application No. PCT/JP99/06309 filed Nov. 12, 1999.

TECHNICAL FIELD

The present invention relates to human protein hAMSH and mouse protein mAMSH, and cDNAs encoding these proteins. More particularly, the present invention relates to novel human and mouse signal transduction molecules, AMSH, human and mouse genes encoding these proteins, cDNAs thereof, and antibodies against these proteins.

BACKGROUND ART

A variety of cells having different functions should collaborate with each other for expression of higher biological functions such as hematopoietic, immunological and nervous systems. Communication among the cells is essential for their collaborations. Cytokines are known to be the proteins responsible for intercellular communication, and include interleukin (IL)-1 to 18, colony stimulation factors (CSFs), interferons (IFNs) and several chemokines.

Signals are generated by binding of the cytokines to specific receptors on the cell membrane, and survival, proliferation, differentiation and functional expression of the cells are controlled by signal transduction. Accordingly, dysfunction of cytokine-receptor signal transduction pathways result in collapse of the immunological and hematopoietic systems to cause severe infectious diseases, cancers and autoimmune diseases.

For the reasons described above, it is quite important to elucidate the intracellular signal transduction pathways mediated by the cytokine/cytokine receptor system. This is important, in order to appreciate the basic phenomena such as proliferation and differentiation of the cells, pathogenesis, diagnosis and therapeutic intervention of various diseases at the molecular levels.

The inventors of the present invention have isolated the genes of "common γ-chain" commonly included in a plurality of the cytokine receptors, and have made a great contribution in elucidating the structure and function of the cytokine receptors. Of particular elucidation is that the γ-chain is an essential subunit for functional expression of IL-2, IL-4, IL-7 and IL-9, and abnormality in the γ-chain causes impairment of early development of T-cells via dysfunction of IL-7 (Science, 262:1874–1877, 1993; Int. Immunol., 6:1451–1454, 1994; Science, 263:1453–1454, 1994; Eur. J. Immunol., 25:3001–3005, 1995).

Recently, the inventors of the present invention have identified "STAMs" as novel signal molecules concerning signal transduction in the proliferating cells by the cytokines, and found that these STAMs are present downstream of the IL-2/GM-CSF receptor and directly associate with JAK3/2. The inventors also found that STAMs play an important role in expression of c-myc and signal transduction for DNA synthesis (Immunity, 6:449–457, 1997).

While several important mechanisms of the intracellular signal transduction pathway by binding of the cytokines to the receptors have been made clear, additional novel molecules should be identified for elucidating the overall structure and function of the intracellular signal transduction pathway, because plural molecules are thought to be continuously and synergetically involved in the signal transduction pathway and to manifest final functional expression by constructing a so-called cascade.

The present invention was performed by taking the above situations into consideration, and the object of this invention is to provide a novel signal transduction molecules interacting with SH3 domain of a signal molecule STAM that has been found by the present inventors, and exerting essential functions on signal transduction to the downstream from STAM.

Another object of the present invention is to provide gene encoding this novel molecule, cDNA thereof, and antibody against the novel molecule.

DISCLOSURE OF INVENTION

The present invention for solving the foregoing problems provides a human protein hAMSH having the amino acid sequence of SEQ ID No. 1

The present invention also provides a human gene encoding the human protein hAMSH, hAMSH cDNA having the nucleotide sequence of SEQ ID No. 2, and a DNA fragment comprising a partial sequence of SEQ ID No. 2.

The present invention further provides a recombinant vector containing the cDNA or the partial fragment thereof, and an antibody against the human protein hAMSH.

The present invention additionally provides a mouse protein mAMSH having the amino acid sequence of SEQ ID No. 3, a mouse gene encoding the mouse protein mAMSH, mAMSH cDNA having the nucleotide sequence of SEQ ID No. 4, a DNA fragment comprising a partial sequence of SEQ ID No. 4, a recombinant vector containing the cDNA or the DNA fragment thereof, and an antibody against the mouse protein mAMSH.

BEST MODE FOR CARRYING OUT THE INVENTION

The procedure for obtaining a human protein hAMSH and cDNA thereof, as well as the procedure for identifying the function of the protein will be described hereinafter.

The human protein hAMSH cDNA according to the present invention is a human gene's cDNA isolated by screening a human cDNA library by Far-Western method using a chimera gene of SH3 domain of STAM gene and glutathione-S-transferase (GST). This cDNA has a nucleotide sequence comprising 1910 base pairs shown in SEQ ID No. 2, and encodes the protein hAMSH having the amino acid sequence of SEQ ID No. 1.

While estimated a nucleus transfer signal and a JAB1-like structure are observed in the molecule of the protein hAMSH, this protein is confirmed to be a novel molecule since corresponding molecules are not found in the protein data base.

The facts that this protein hAMSH is a novel molecule involved in signal transduction for cell proliferation by association with STAM, downstream of the cytokine receptor, is confirmed as follows:

(1) AMSH-dc2 in which half of the C-terminal region of hAMSH has been deleted, suppresses signal transduction for DNA synthesis after stimulating with IL-2 and GM-CSF; and (2) The AMSH-dc2 mutant suppresses c-myc inducing signal transduction after stimulating with IL-2 and GM-CSF.

The cDNA of the mouse protein nAMSH according to the present invention is a mouse gene's cDNA isolated by screening a mouse cDNA library using the hAMSH cDNA as a probe. This cDNA has the nucleotide sequence comprising 1384 base pairs shown in SEQ ID No. 4, and encodes the protein mAMSH having the amino acid sequence of SEQ ID No. 3.

The proteins hAMSH and mAMSH according to the present invention may be obtained by conventional methods such as isolating from human or mouse organs or from cell lines, preparing the peptides by a chemical synthesis based on the amino acid sequence provided by the present invention, or by a recombinant DNA techniques using the cDNA fragments provided by the present invention. For example, in order to obtain the protein hAMSH by the recombinant DNA technique, RNA is prepared by in vitro transcription from the vectors comprising cDNA fragment having the nucleotide sequence of SEQ ID No. 2, and the protein may be expressed through in vitro translation using the RNA as a template. The protein encoded by the cDNA may be also expressed in large scale in *E. coli, Bacillus subtilis*, yeast, animal cells and plant cells by recombining an expression vector with the translation region of cDNA by known methods in the art.

When the protein according to the present invention is produced by expression of DNA by in vitro translation, the cDNA or its translation region is recombined into a vector having a RNA polymerase promoter, and the recombinant cDNA is added in an in vitro translation system such as a rabbit dyalyzate or wheat germ extract containing a RNA polymerase for the promoter. Examples of the RNA polymerase promoter include T6, T3 and SP6. Examples of the vector containing these RNA polymerase promoter include pKA1, pCDM8, pT3/7 18, pT7/3 19 and pBlueprint II.

For large scale production of the protein encoded in cDNA in microorganisms such as *E. coli*, an expression vector is constructed by inserting the cDNA according to the present invention or its translation region into an expression vector comprising an origin suitable for microorganisms, a promoter, a ribosome binding site, cDNA cloning sites and terminater, followed by cultivation of the transformant cell obtained after translormation of the host cell with the expression vector. A protein containing an arbitrary region can be obtained by allowing the expression vector to express by adding an initiation codon and a stop codon before and after the arbitrary translation region. Otherwise, a desired protein portion can be selectively obtained by allowing the protein to express as a fusion protein with other protein, followed by cleaving this fusion protein with an appropriate protease. Examples of the expression vector for use in *E. coli* include pUC, pBluescript II, pET expression system and pGEX expression system.

For producing the protein according to the present invention in eukaryotic cell such as animal cells, the cDNA or the translation region thereof is inserted into an expression vector for the eukaryotic cell comprising a promoter, splicing region and poly (A) addition site to introduce the recombinant vector into the eukaryotic cell. Examples of the expression vector include pKA1, pCDM8, pSVK3, pMSG, pSVL, pBK-CMV, pBK-RSV, EBV vector, pRS and pYES2. While cultured cells of a mammal such as monkey kidney cells COS7 and Chinese hamster ovary cells CHO, budding yeast, dividing yeast, silkworm cells and African clawed frog egg cells are usually used as the eukaryotic cells, any eukaryotic cells may be used so long as they are able to express MIST. The expression vector can be introduced into the eukaryotic cell by a conventional method such as an electroporation method, a calcium phosphate method, a liposome method and a DEAE dextran method.

Separation procedures known in the art may be combined for isolating and purifying the desired protein from the culture after expressing the protein in microorganisms or eukaryotic cells. The separation and purifying methods include, for example, treatment with a denaturation reagent such as urea or with a surface active agent, ultrasonic treatment, enzymatic digestion, salting-out and solvent precipitation method, dialysis, centrifugation, ultrafiltration, gel filtration, SDS-PAGE, isoelectric point electrophoresis, ion exchange chromatography, hydrophobic chromatography, affinity chromatography and reversed phase chromatography.

Peptide fragments (five amino acid residues or more) containing any partial amino acid sequence of the amino acid sequence of SEQ ID Nos 1 and 3 are included in the proteins hAMSH and mAMSH according to the present invention. These peptide fragments may be used for producing antibodies. Fusion proteins with other proteins are also included in the protein according to the present invention.

The gene of the present invention is a human gene encoding the protein described above, and can be isolated, for example, from the existing genome library using the cDNA of the present invention or a partial sequence thereof as a probe.

The cDNA of the present invention may be obtained by screening a cDNA library derived from a human cell or mouse cell through colony or plaque hybridization known in the art by using the oligonucleotide probe synthesized, based on the nucleotide sequence of SEQ ID Nos. 2 and 4. Alternatively, the cDNA of the present invention can be prepared from the mRNA isolated from a human cell or mouse cell by the RT-PCR method using synthesized oligonucleotides that can hybridize to both ends of the cDNA fragment as primers.

Polymorphism due to individual differences is often observed in the animal gene. Accordingly, cDNAs containing an addition or deletion of one or plural nucleotides, and/or substitution with other nucleotides in SEQ ID Nos. 2 and 4 are also included within the scope of the present invention.

Likewise, the proteins containing an addition or deletion of one or plural amino acids, and/or substitution with other amino acids caused by the alteration of cDNAs may be also included within the scope of the present invention, provided that the protein comprises protein activity pf the protein having the amino acid sequence of SEQ ID No. 1 or 3.

The DNA fragments (10 bp or more) comprising any partial nucleotide sequence of SEQ ID No. 2 or 4 are also included in the DNA fragment of the present invention. DNA fragments comprising sense strand and antisense strand may be categorized into the DNA fragment of the present invention. The DNA fragments can be used as a probe for gene diagnosis.

Antibodies against the proteins of the present invention may be obtained as polyclonal antibodies or monoclonal antibodies by conventional methods using the proteins themselves or partial peptides thereof as antigens.

EXAMPLE

A part of the hAMSH cDNA (the 383–550th in SEQ ID No. 2: corresponds to the amino acids 125–180th in SEQ ID No. 1) was amplified by PCR and was inserted into the GST fusion protein expression vector. This vector was introduced into *E coli* for transformation, and this transformant was stimulated with IPTG to induce expression of the GST fusion protein. The induced fusion protein was purified by affinity chromatography using a glutathione column, thereby obtaining the GST fusion protein. An antiserum was obtained by immunizing a rabbit with this GST fusion protein as an antigen.

INDUSTRIAL APPLICABILITY

As hitherto described in detail, the present invention provides novel signal transduction molecules related to the cytokine based signal transduction pathway, and gene engineering materials. These molecules and gene engineering materials are useful for developing diagnostic and therapeutic methods as well as pharmaceuticals for human diseases due to dysfunction of the cytokine based signal transduction pathway such as severe infectious diseases, cancers and autoimmune diseases.

What is claimed is:

1. An isolated mouse protein mAMSH having the amino acid sequence of SEQ ID NO: 3.

2. An isolated mouse gene encoding the mouse protein mAMSH having the amino acid sequence of SEQ ID No. 3.

3. A cDNA of the mouse gene of claim 2, which is mAMSH cDNA having the nucleotide sequence of SEQ ID No. 4.

4. A recombinant vector containing the mAMSH cDNA of claim 3.

* * * * *

SEQUENCE LISTING

<160> NUMBER OF SEQ ID NOS: 4

<210> SEQ ID NO 1
<211> LENGTH: 424
<212> TYPE: PRT
<213> ORGANISM: Homo sapiens

<400> SEQUENCE: 1

Met Ser Asp His Gly Asp Val Ser Leu Pro Pro Glu Asp Arg Val Arg
 1               5                  10                  15

Ala Leu Ser Gln Leu Gly Ser Ala Val Glu Val Asn Glu Asp Ile Pro
            20                  25                  30

Pro Arg Arg Tyr Phe Arg Ser Gly Val Glu Ile Ile Arg Met Ala Ser
        35                  40                  45

Ile Tyr Ser Glu Glu Gly Asn Ile Glu His Ala Phe Ile Leu Tyr Asn
    50                  55                  60

Lys Tyr Ile Thr Leu Phe Ile Glu Lys Leu Pro Lys His Arg Asp Tyr
65                  70                  75                  80

Lys Ser Ala Val Ile Pro Glu Lys Lys Asp Thr Val Lys Lys Leu Lys
                85                  90                  95

Glu Ile Ala Phe Pro Lys Ala Glu Glu Leu Lys Ala Glu Leu Leu Lys
            100                 105                 110

Arg Tyr Thr Lys Glu Tyr Thr Glu Tyr Asn Glu Glu Lys Lys Lys Glu
        115                 120                 125

Ala Glu Glu Leu Ala Arg Asn Met Ala Ile Gln Gln Glu Leu Glu Lys
    130                 135                 140

Glu Lys Gln Arg Val Ala Gln Gln Lys Gln Gln Gln Leu Glu Gln Glu
145                 150                 155                 160

Gln Phe His Ala Phe Glu Glu Met Ile Arg Asn Gln Glu Leu Glu Lys
                165                 170                 175

Glu Arg Leu Lys Ile Val Gln Glu Phe Gly Lys Val Asp Pro Gly Leu
            180                 185                 190

Gly Gly Pro Leu Val Pro Asp Leu Glu Lys Pro Ser Leu Asp Val Phe
        195                 200                 205

Pro Thr Leu Thr Val Ser Ser Ile Gln Pro Ser Asp Cys His Thr Thr
    210                 215                 220

```
Val Arg Pro Ala Lys Pro Pro Val Val Asp Arg Ser Leu Lys Pro Gly
225                 230                 235                 240

Ala Leu Ser Asn Ser Glu Ser Ile Pro Thr Ile Asp Gly Leu Arg His
            245                 250                 255

Val Val Val Pro Gly Arg Leu Cys Pro Gln Phe Leu Gln Leu Ala Ser
            260                 265                 270

Ala Asn Thr Ala Arg Gly Val Glu Thr Cys Gly Ile Leu Cys Gly Lys
        275                 280                 285

Leu Met Arg Asn Glu Phe Thr Ile Thr His Val Leu Ile Pro Lys Gln
290                 295                 300

Ser Ala Gly Ser Asp Tyr Cys Asn Thr Glu Asn Glu Glu Leu Phe
305                 310                 315                 320

Leu Ile Gln Asp Gln Gln Gly Leu Ile Thr Leu Gly Trp Ile His Thr
                325                 330                 335

His Pro Thr Gln Thr Ala Phe Leu Ser Ser Val Asp Leu His Thr His
            340                 345                 350

Cys Ser Tyr Gln Met Met Leu Pro Glu Ser Val Ala Ile Val Cys Ser
        355                 360                 365

Pro Lys Phe Gln Glu Thr Gly Phe Phe Lys Leu Thr Asp His Gly Leu
370                 375                 380

Glu Glu Ile Ser Ser Cys Arg Gln Lys Gly Phe His Pro His Ser Lys
385                 390                 395                 400

Asp Pro Pro Leu Phe Cys Ser Cys Ser His Val Thr Val Val Asp Arg
                405                 410                 415

Ala Val Thr Ile Thr Asp Leu Arg
                420

<210> SEQ ID NO 2
<211> LENGTH: 1910
<212> TYPE: DNA
<213> ORGANISM: Homo sapiens
<220> FEATURE:
<221> NAME/KEY: CDS
<222> LOCATION: 11..1282

<400> SEQUENCE: 2
cttggtcctg atgtctgacc atggagatgt gagcctcccg cccgaagacc gggtgagggc      60
tctctcccag ctgggtagtg cggtagaggt gaatgaagac attccacccc gtcggtactt     120
ccgctctgga gttgagatta tccgaatggc atccatttac tctgaggaag caacattga     180 acatgccttc atcctctata caagtatatc acgctctttt attgagaaac taccaaaaca     240
tcgagattac aaatctgctg tcattcctga aagaaagac acagtaaaga aattaaagga     300
gattgcattt cccaaagcag aagagctgaa ggcagagctg ttaaaacgat ataccaaaga     360
atatacagaa tataatgaag aaaagaagaa ggaagcagag gaattggccc ggaacatggc     420
catccagcaa gagctggaaa aggaaaaaca gagggtagca caacagaagc agcagcaatt     480
ggaacaggaa cagttccatg ccttcgagga gatgatccgg aaccaggagc tagaaaaaga     540
gcgactgaaa attgtacagg agtttgggaa ggtagaccct ggcctaggtg gcccgctagt     600
gcctgacttg gagaagccct ccttagatgt gttcccccacc ttaacagtct catccataca     660
gccttcagac tgtcacacaa ctgtaaggcc agctaagcca cctgtggtgg acaggtcctt     720
gaaacctgga gcactgagca actcagaaag tattcccaca atcgatggat tgcgccatgt     780
ggtggtgcct gggcggctgt gcccacagtt tctccagtta gccagtgcca acactgcccg     840
```

-continued

```
gggagtggag acatgtggaa ttctctgtgg aaaactgatg aggaatgaat ttaccattac    900
ccatgttctc atccccaagc aaagtgctgg gtctgattac tgcaacacag agaacgaaga    960
agaacttttc ctcatacagg atcagcaggg cctcatcaca ctgggctgga ttcatactca   1020
ccccacacag accgcgtttc tctccagtgt cgacctacac actcactgct cttaccagat   1080
gatgttgcca gagtcagtag ccattgtttg ctcccccaag ttccaggaaa ctggattctt   1140
taaactaact gaccatggac tagaggagat ttcttcctgt cgccagaaag gatttcatcc   1200
acacagcaag gatccacctc tgttctgtag ctgcagccac gtgactgttg tggacagagc   1260
agtgaccatc acagaccttc gatgagcgtt tgagtccaac ccttccaag aacaacaaaa    1320
ccatatcagt gtactgtagc cccttaattt aagctttcta gaaagctttg gaagtttttg   1380
tagatagtag aaagggggc atcacctgag aaagagctga ttttgtattt caggtttgaa    1440
agaaataac tgaacatatt ttttaggcaa gtcagaaaga gaacatggtc acccaaaagc    1500
aactgtaact cagaaattaa gttactcaga aattaagtag ctcagaaatt aagaaagaat   1560
ggtataatga acccccatat acccttcctt ctggattcac caattgttaa cattttttc    1620
ctctcagcta tccttctaat ttctctctaa tttcaatttg tttatattta cctctgggct   1680
caataagggc atctgtgcag aaatttggaa gccatttaga aaatcttttg gattttcctg   1740
tggtttatgg caatatgaat ggagcttatt actggggtga gggacagctt actccatttg   1800
accagattgt ttggctaaca catcccgaag aatgattttg tcaggaatta ttgttattta   1860
ataaatattt caggatattt ttcctctaca ataaagtaac aattaactta              1910
```

<210> SEQ ID NO 3
<211> LENGTH: 424
<212> TYPE: PRT
<213> ORGANISM: mouse

<400> SEQUENCE: 3

```
Met Ser Asp His Gly Asp Val Ser Leu Pro Pro Gln Asp Arg Val Arg
  1               5                  10                  15

Ile Leu Ser Gln Leu Gly Ser Ala Val Glu Leu Asn Glu Asp Ile Pro
             20                  25                  30

Pro Arg Arg Tyr Tyr Arg Ser Gly Val Glu Ile Ile Arg Met Ala Ser
         35                  40                  45

Val Tyr Ser Glu Glu Gly Asn Ile Glu His Ala Phe Ile Leu Tyr Asn
     50                  55                  60

Lys Tyr Ile Thr Leu Phe Ile Glu Lys Leu Pro Lys His Arg Asp Tyr
 65                  70                  75                  80

Lys Ser Ala Ile Ile Pro Glu Lys Lys Asp Ala Val Lys Lys Leu Lys
                 85                  90                  95

Ser Val Ala Phe Pro Lys Ala Glu Glu Leu Lys Thr Glu Leu Leu Arg
            100                 105                 110

Arg Tyr Thr Lys Glu Tyr Glu Gln Tyr Lys Glu Arg Lys Lys Lys Glu
        115                 120                 125

Glu Glu Glu Leu Ala Arg Asn Ile Ala Ile Gln Glu Leu Glu Lys
    130                 135                 140

Glu Lys Gln Arg Val Ala Gln Lys Gln Gln Leu Glu Gln Glu
145                 150                 155                 160

Gln Phe His Ala Phe Glu Glu Met Ile Gln Arg Glu Leu Glu Lys
                165                 170                 175

Glu Arg Leu Lys Ile Val Gln Glu Phe Gly Lys Val Asp Pro Gly Pro
            180                 185                 190
```

-continued

Cys Gly Pro Leu Leu Pro Asp Leu Glu Lys Pro Cys Val Asp Val Ala
         195                 200                 205

Pro Ser Ser Pro Phe Ser Pro Thr Gln Thr Pro Asp Cys Asn Thr Gly
    210                 215                 220

Met Arg Pro Ala Lys Pro Pro Val Val Asp Arg Ser Leu Lys Pro Gly
225                 230                 235                 240

Ala Leu Ser Val Ile Glu Asn Val Pro Thr Ile Glu Gly Leu Arg His
                245                 250                 255

Ile Val Val Pro Arg Asn Leu Cys Ser Glu Phe Leu Gln Leu Ala Ser
            260                 265                 270

Ala Asn Thr Ala Lys Gly Ile Glu Thr Cys Gly Val Leu Cys Gly Lys
        275                 280                 285

Leu Met Arg Asn Glu Phe Thr Ile Thr His Val Leu Ile Pro Arg Gln
    290                 295                 300

Asn Gly Gly Pro Asp Tyr Cys His Thr Glu Asn Glu Glu Ile Phe
305                 310                 315                 320

Phe Met Gln Asp Leu Gly Leu Leu Thr Leu Gly Trp Ile His Thr
                325                 330                 335

His Pro Thr Gln Thr Ala Phe Leu Ser Ser Val Asp Leu His Thr His
            340                 345                 350

Cys Ser Tyr Gln Met Met Leu Pro Glu Ser Ile Ala Ile Val Cys Ser
        355                 360                 365

Pro Lys Phe Gln Glu Thr Gly Phe Phe Lys Leu Thr Asp Tyr Gly Leu
    370                 375                 380

Gln Glu Ile Ser Thr Cys Arg Gln Lys Gly Phe His Pro His Gly Arg
385                 390                 395                 400

Asp Pro Pro Leu Phe Cys Asp Cys Ser His Val Thr Val Lys Asp Arg
                405                 410                 415

Ile Val Thr Ile Thr Asp Leu Arg
            420

<210> SEQ ID NO 4
<211> LENGTH: 1384
<212> TYPE: DNA
<213> ORGANISM: homo sapiens
<220> FEATURE:
<221> NAME/KEY: CDS
<222> LOCATION: 56..1327

<400> SEQUENCE: 4
gtgacgtttc cggaagctct gactgtcatc cttcacgaaa gaacttattt gtccaatgtc     60
tgaccatggg gatgtgagcc tcccacccca agaccgggtg aggattctgt cccaacttgg    120
gagtgcagtt gagttaaatg aagacattcc accccgtcgc tactaccgct ccggtgttga    180
gatcatccgc atggcgtccg tttactcgga agaaggcaac attgaacatg cctttatcct    240
ctacaacaag tacatcacgc tgtttattga aaaacttccg aaacaccgag actacaaatc    300
agctatcatt cctgagaaga agatgctgt caagaaatta agagcgtcg ctttccctaa    360 agcggaagag ctgaagacag agctcttgag aagatacacc aaagaatatg agcagtataa    420
agagcgaaag aaaaaggaag aagaggaact tgcccgaaat atcgccatcc agcaagagtt    480
ggaaaaagaa aaacagaggg ttgctcagca gaagcagaag cagctagagc aggagcaatt    540
ccatgccttt gaggagatga tccagaggca ggagctggaa aaagaacggc tgaaaattgt    600
tcaagagttc gggaaggtag accctggccc ctgcgggcct ctgctccctg atctggaaaa    660

-continued

| | | | | |
|---|---|---|---|---|
| gccttgtgta | gatgtggccc | ccagctcacc | gttctcgccc | acgcagactc cagactgtaa 720 |
| cacaggcatg | aggccagcta | agccacctgt | ggtggacagg | tccctgaaac ctggagcgtt 780 |
| aagcgtcata | gaaaatgttc | ccaccattga | aggcctgcgc | cacatcgtgg tgccccgtaa 840 |
| tctgtgctca | gaatttctcc | agcttgccag | tgccaatacc | gccaaaggca ttgaaacctg 900 |
| tggagtcctc | tgtggaaaac | tgatgagaaa | tgaattcaca | atcacacatg ttctcatccc 960 |
| cagacaaaat | ggtgggcctg | attattgcca | cacggagaat | gaagaagaaa ttttctttat 1020 |
| gcaggatgac | cttggactcc | tcactcttgg | ctggatccat | actcatccaa cccaaacggc 1080 |
| ctttctgtcc | agtgtggatc | tccacactca | ctgctcctac | caaatgatgt taccagagtc 1140 |
| catcgcaatc | gtctgttccc | caaagttcca | ggaaactgga | ttctttaagc taactgacta 1200 |
| tggtcttcaa | gagatttcaa | cctgccggca | gaaaggcttt | caccccatg gcagagaccc 1260 |
| accgctgttc | tgtgactgca | gccatgtcac | tgtcaaggac | agaattgtga cgatcacaga 1320 |
| ccttcgataa | atctcaaatc | atgaaccagg | gagatggatc | actgggtaac agcacttgtc 1380 |
| acca | | | | 1384 |